US005907592A

United States Patent [19]
Levinson

[11] Patent Number: 5,907,592
[45] Date of Patent: May 25, 1999

[54] AXIALLY INCREMENTED PROJECTION DATA FOR SPIRAL CT

[76] Inventor: Reuven Levinson, c/o Ralph Levinson, 11 Curtis Pkwy, Kenmore, N.Y. 14217

[21] Appl. No.: 08/550,642

[22] Filed: Oct. 31, 1995

[51] Int. Cl.$^6$ .................................................. H01J 35/10
[52] U.S. Cl. .................................................. 378/4; 378/144
[58] Field of Search .................................. 378/4, 11, 12, 378/13, 14, 25, 24, 145, 146, 138, 137, 143, 144

[56] References Cited

U.S. PATENT DOCUMENTS

| | | | |
|---|---|---|---|
| 3,836,804 | 9/1974 | Frens et al. | 378/144 |
| 4,991,194 | 2/1991 | Laurent et al. | 378/143 |
| 5,224,136 | 6/1993 | Toth et al. | 378/146 |

*Primary Examiner*—David P. Porta
*Attorney, Agent, or Firm*—Benjamin J. Barish

[57] ABSTRACT

A method and apparatus for examining an object by rotating a radiant energy generator around the object while projecting a beam of radiant energy towards the object to impinge the object at a plurality of angles in each of a plurality of planes substantially perpendicular to the z-axis, and detecting radiant energy leaving the object after impinging same, to produce sets of projection measurements representing slices of the object in the planes. During rotation of the radiant energy generator, the radiant energy beam is sequentially modulated between two locations along the z-axis to produce, during each rotation of the generator, two sets of projection measurements representing two slices of the object, which projection measurements are used in an interlaced manner for reconstructing the image of the object.

5 Claims, 3 Drawing Sheets

AXIALLY INCREMENTED PROJECTION DATA FOR SPIRAL CT

BACKGROUND OF THE INVENTION

1. Field of the Invention

The invention is a radiography apparatus to be used for computerized tomography. More specifically, this invention relates to an x-ray tube, beam collimation and data collection system to be used with a computerized tomograph in spiral scanning.

2. Description of the Prior Art

Computerized Tomography (CT) is a standard imaging technique in the radiology clinic. Spiral CT scanning is a technique, whereby the patient is transported through the x-ray beam during continuous rotation of the x-ray beam. The spiral technique results in a significant reduction in examination times versus the conventional CT slice-by-slice technique.

Trade-offs between volume coverage, scan time and image time quality are required in the selection of the spiral CT scan parameters-exposure technique factors, slice width, and patient table speed. In particular, the scanned volume may be increased with no increase in scan time through the use of faster table speed, however the faster speeds result in larger slice sensitivity profiles and reduced Z-dimension spatial resolution of the CT images.

While it is desirable to decrease the scan time for a given volume, or conversely increase the volume coverage for a given scan time through the use of faster table speeds, there is a reduction in image quality with the use of higher table speeds. The influence of table speed or pitch (slice width/ table speed) on image quality has been documented in the literature (Polacin et al, Radiology 1992; 185:29–35). In particular, the use of pitch values greater than 1 results in severe broadening of the slice sensitivity profiles. The use of 180° interpolation schemes serves to reduce the broadening of the slice sensitivity profiles at the cost of higher image noise. However, even with 180° interpolation, there is still slice sensitivity profile broadening for large pitch values. For example, Polacin et al report a 30 percent slice sensitivity profile broadening with pitch=2 and a 180° linear interpolation (LI).

Spiral CT examinations, due to their short scan times and reduced patient motion, produce superior multi-planar reformations (MPR) and 3D images. In addition, spiral CT has also enabled the development of CT angiography. The image quality of MPR, 3D and MIP (maximum intensity projection) images is dependent on the image quality of the axial CT slices. In particular, the Z-dimension spatial resolution of MPR, 3D and MIP images is dependent on the slice sensitivity profile of the axial CT images and the spacing of the axial CT images. Conflicting desires are encountered to obtain maximum scan volume coverage (i.e. maximum Z-dimension scan length) while simultaneously preserving high Z-dimension spatial resolution. In particular, spiral examinations with high pitch values enable large scan volume coverage, however the slice sensitivity profiles broadening of the axial CT slices reduces the Z-dimensional spatial resolution of the MPR, 3D and MIP images.

There remains, therefore, a need for method and apparatus to enable large volume acquisitions while preserving minimal scan times while simultaneously maintaining high Z-dimensional spatial resolution. In addition, there is a need for a method and apparatus to enable large volume acquisitions and high Z-dimension spatial resolution for MPR, 3D and MIP images.

There is further need for such a method and apparatus which is compatible with existing computerized tomography systems and is economical to manufacture and use.

SUMMARY OF THE INVENTION

This radiographic apparatus consists of an x-ray tube combined with a beam collimator, data acquisition system and interpolation algorithm. This apparatus is to be used with 3rd and 4th generation spiral CT systems. The anode of the x-ray tube contains radially-oriented sectors. These sectors modulate the z-position of the focal spot of the x-ray beam to two positions. The beam collimation collimates the x-ray beam from the two positions of the focal spot. The data acquisition system measures the radiation transmitted through the scanned object and sorts the measurements by focal spot position and gantry rotation angle about the scanned object. The modulation of the position of the focal spot (in the z-direction) enables the CT system to measure in a 360° gantry rotation 2 sets of projection data. The 2 sets of projection data are offset which respect to each other in the z-direction. The two sets of projection data are synthesized into planar data sets from which the axial images are reconstructed.

An object of this invention is to provide a method and apparatus which enable large pitch spiral scanning with minimal broadening of the slice sensitivity profile.

Another object of this invention is to provide a method and apparatus which enable high value pitch spiral scanning with overlapping axial slice reconstructions and high Z-dimension spatial resolution MPR, 3D and MIP images.

A further object of this invention is to provide such a method and apparatus wherein improved axial CT image quality and MPR, 3D and MIP CTA (CT angiography) are provided without the need for substantial increase in radiation exposure levels.

According to one aspect of the present invention, there is provided a method of examining an object comprising: translating the object along a z-axis; rotating a radiant energy generator around the object while projecting a beam of radiant energy towards the object to impinge the object at a plurality of angles in each of a plurality of planes substantially perpendicular to the z-axis; detecting radiant energy leaving the object after impinging same, to produce sets of projection measurements representing slices of the object in the planes; and utilizing the projection measurements to reconstruct an image of the object corresponding to the detected radiant energy. During rotation of the radiant energy generator, each radiant energy beam projected thereby is sequentially modulated between a plurality of "n" locations along the z-axis to produce, during each rotation of the generator, "n" sets of projection measurements representing "n" slices of the object at the "n" z-axis locations; and the "n" sets of projection measurements are utilized in an interlaced manner for reconstructing the image of the object.

According to further features in the described preferred embodiment, "n"=2, i.e., two sets of projection measurements are produced and interlaced. In addition, the radiant energy generator has a rotating part divided into a plurality of equal-width sectors of stepped formation defining high surfaces at a first location along the z-axis alternating with low surfaces at a second location along the z-axis different from the first location, the stepped surfaces modulating the generated radiant energy beam between two z-axis locations during the rotation of the radiant energy generator.

According to still further features in the described preferred embodiment, the rotating part of the radiant energy generator is an anode which is impinged by an electron beam to generate fan-shaped x-ray beams. The rotating part is divided into a first plurality of sectors alternating with a second plurality of sectors of the same width but of a different thickness as the first plurality of sectors, all the sectors being impinged by the electron beam to alternatingly displace the generated x-ray beams with respect to the z-axis during each rotation of the anode. Preferably, the two plurality of sectors are dimensioned to produce a 50% ovelap in the generated x-ray beams.

The invention also provides apparatus for examining objects in accordance with the above method.

DESCRIPTION OF THE PREFERRED EMBODIMENTS

As used herein, the term "object" or words of similar import will refer to various types of objects through which it is desired to pass radiation for testing and/or diagnostic purposes including, but not limited to humans and animals, specimens removed from humans and animals, non-destructive testing and security purposes. While for purposes of clarity specific reference will be made herein to a preferred use in medical environments, it will appreciated that other forms of objects may be employed in connection with the apparatus of this invention in addition to medical uses and such other uses are expressly contemplated As used herein, the term "scanner" and words of similar import shall mean a CT scanner capable of performing spiral (sometimes called helical) CT examinations.

Figure 1:
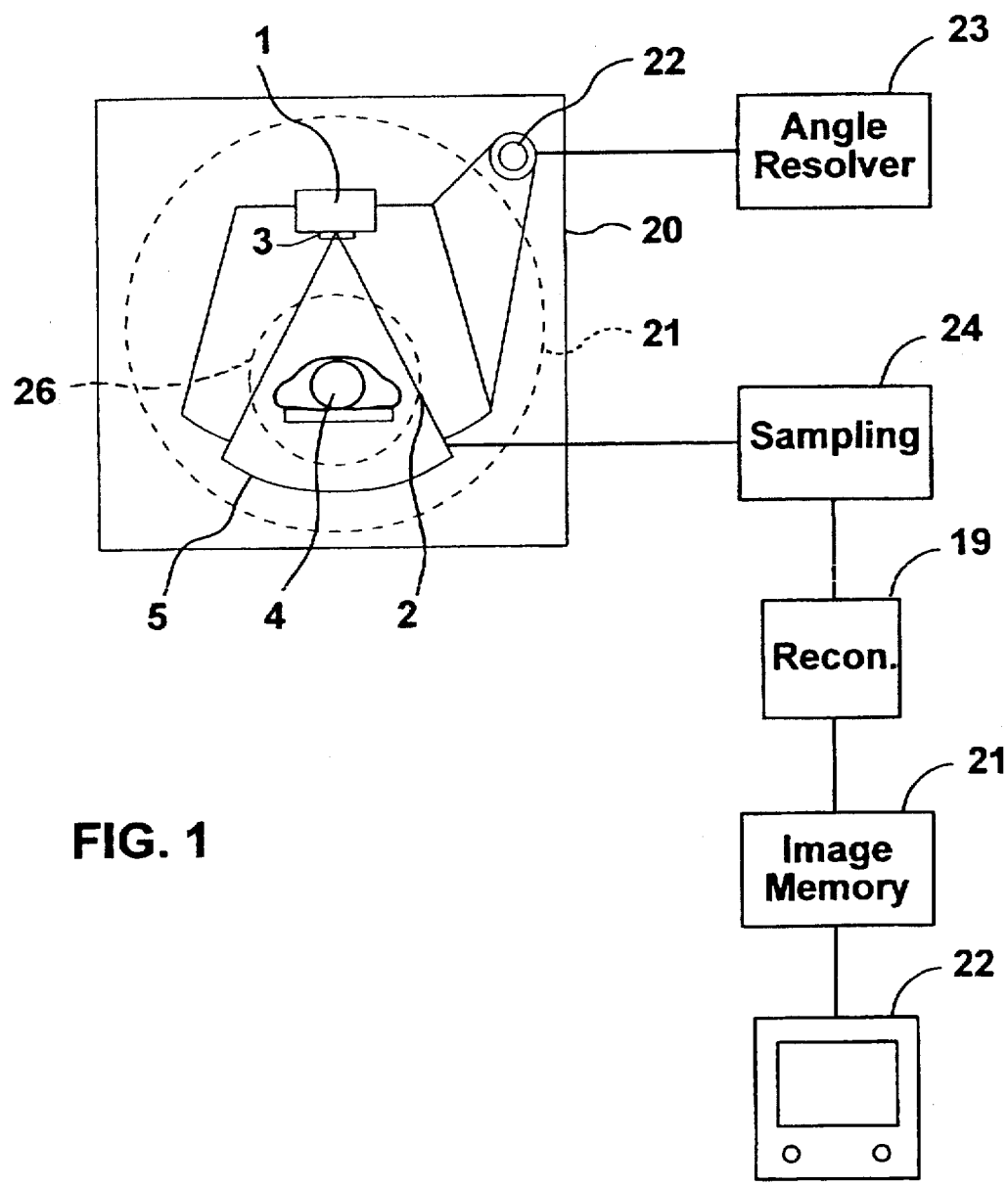
FIG. 1 is a schematic illustration of a form of CT system of the present invention wherein the x-ray tube, beam collimation and data acquisition system are integrated into a 3rd generation CT system.

Referring now to FIG. 1 there is shown a CT gantry containing an x-ray tube 1. The x-ray tube emits a beam 2 which in collimated into a fan shape by the beam collimation system 3, impinges on the object 4, which in the form shown is a patient. The beam 2 which has passed through the patient impinges on the x-ray detector system 5.

Figure 2:
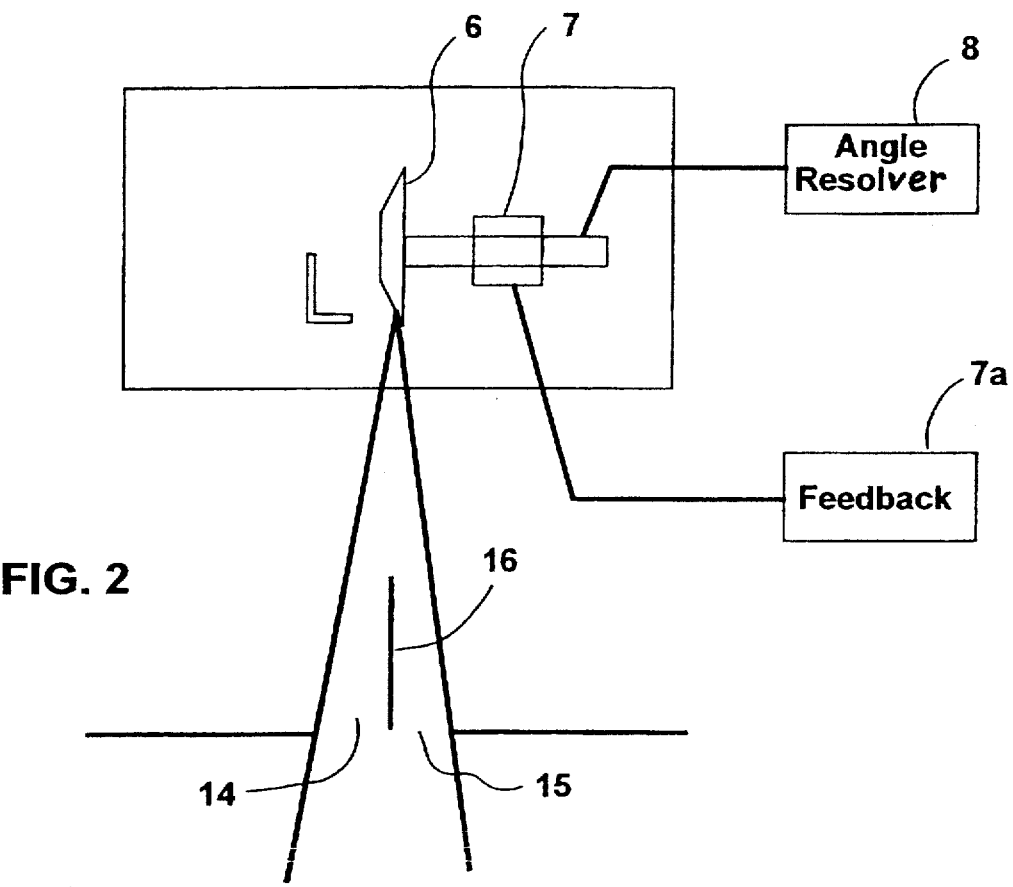
FIG. 2 is a schematic illustration of the x-ray tube and the beam collimation.

Referring now to FIG. 2 there is shown the x-ray tube. The tube contains a rotating anode 6. The stator assembly 7 includes a drive which rotates the anode. There is shown at 8 a means to measure the angular displacement of the anode and the rotational speed of the anode. The stator contains a feedback mechanism 7a that receives input from the angular resolver means 8 and regulates the rotational speed of the anode. There is also shown the beam collimator 3 together with the x-ray tube. The beam collimator contains two slits 14 and 15 and a collimation wall 16.

Figure 3:
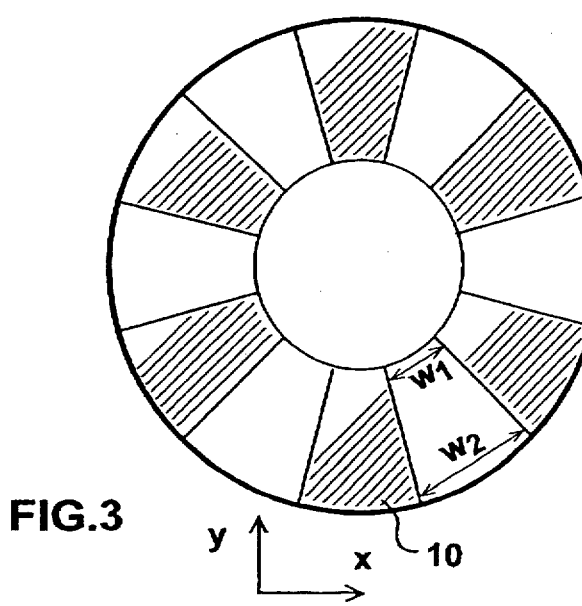
FIGS. 3 and 4 are front and side schematic illustrations, respectively.
Figure 4:
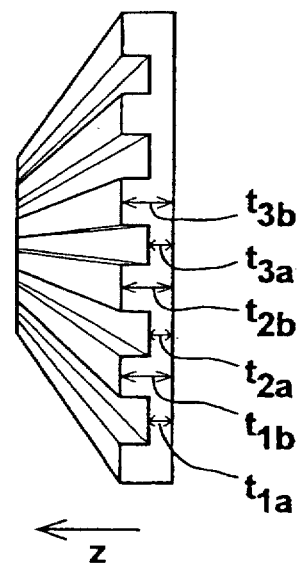

Referring now to FIGS. 3 and 4 there is shown the anode 6 of the x-ray tube. The anode contains radially-oriented regions or sectors 10. The surface dimensions ($w_1$, $w_2$, 1) of all the secors are identical. The difference in the thickness of the anode for adjacent radial regions is constant for all the regions:

$$t_{1b} - t_{1a} = t_{1b} - t_{2a} = t_{2b} - t_{2a} =$$

Every other radial sector has the same anode thickness:

$$t_{1a} = t_{2a} = t_{3a} = \ldots ; t_{1b} = t_{2b} = t_{3b} =$$

Referring again to FIG. 1 there is shown the stationary portion of the gantry 20 and a rotating gantry portion 21. The stationary gantry portion includes a stationary cylinder 26 in which the object to be imaged is received. A motor 22 rotates the rotatable gantry portion 21 around the object 4. The x-ray tube 1 is mounted to the rotatable gantry. In the preferred embodiment the radiation detectors 5 are mounted on the rotating gantry to rotate with the radiation source. Alternately, the radiation detectors can be arranged in complete circle on the stationary gantry portion. An angular position monitoring means or resolver 23 monitors the angular position of the x-ray tube beam relative to the object 4.

Each of the radiation detectors 5 is connected with a sampling means 24. Each time the z-position of x-ray focal spot position is changed (by the rotation of the anode) the detectors are sampled, In addition, each time the x-ray source and detectors rotate a preselected angular increment relative to the object 4 the detectors are sampled. In this manner, the electronic data that is collected represents the radiation attenuation along a preselected multiplicity of paths, via each anode sector 10 through the object to the detectors. A reconstruction means 19 reconstructs the radiation attenuation data using a filtered back projection or other conventional algorithm into an image representation which is stored in an image memory 21 for display on a video monitor 22.

The sampling means 24 is triggered by the angular resolver means 23 such that when the electron beam is fully incident on one anode sector the sampling begins. When the electron beam reaches the end of the sector, due to the rotation of the anode, the angular resolver means 23 again triggers the sampling means 24 to terminate the data collection. The detectors are reset while the electron beam transverses the border between the anode sectors. When the entire electron beam is incident on the next sector, the angular resolver means 23 triggers the end of the reset and the initiation of the next sampling. For each preselected angular increment of the x-ray source relative to the patient, two data samples are collected from two adjacent anode sectors, i.e., from two the x-ray focal spot positions (two different z-coordinates).

Figure 5:
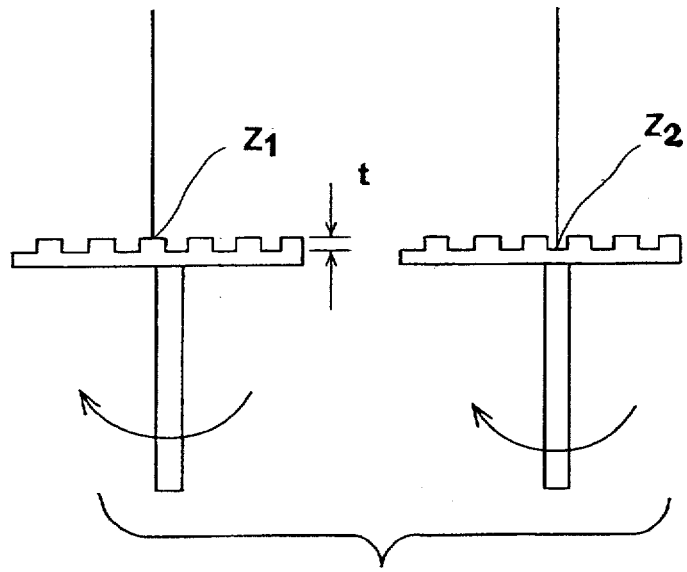
FIG. 5 is a schematic illustration of the electron beam and anode of the x-ray tube, bottom view.

Referring now to FIG. 5 there are shown the two focal spot locations, $z_1$ and $z_2$. The two locations have identical x, y coordinates. The difference in the z-coordinate is "t". The z-position of the focal spot varies as the anode rotates, due to the difference in thickness of the adjacent anode sector. The alternating anode sectors modulate the z-position of the focal spot by t.

Figure 6:
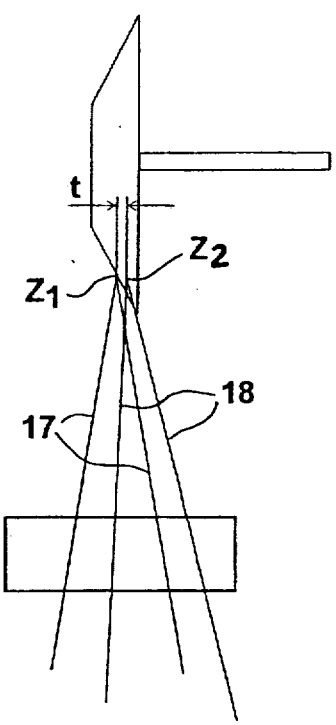
FIG. 6 is a schematic illustration of the anode of the x-ray tube, the x-ray beam the scanned object.

Referring now to FIG. 6 it is shown that the focal spot modulation enables the CT system to measure projection data for two object volumes 17 (focal spot=$z_1$) and 18 (focal spot=$z_2$). The rotational velocity of the anode is:

Omega=2*Theta/T where

Theta=360°/M and

T=Time for 360° gantry scan/N

M=Number of anode sectors

N=Number of angular samples per 360° scan

P(n) are projection measurements from a multiplicity of angles around the object. Whereas a conventional CT system (with an angular sample density of N) measures N projections per 360° of gantry rotation (with a constant Z-position of the focal spot), the present invention will measure 2N projections for 360° of gantry rotation:

$P(2n+1)[n=0,(N-1)/2]$-projection measurements from focal spot position $z_1$ and $P(2n)[n=1,N/2]$-projection measurements from focal spot $z_2$.

The gantry rotation angles of the two sets of projection measurements, P(2n+1) and P(2n) are interlaced such that the gantry rotation of angle of the $z_1$ projection measurements (P(2n+1)) is midway between the gantry rotation angle of the $z_2$ projection measurements (P(2n)) and the P(2n) measurements are midway between the P(2n+1) measurements.

Referring to FIG. 6 the relationship between 17 and 18 is determined by the focal spot-detector distance, focal spot-isocenter distance and t. Though any selection may be made for t, the selection that results in a 50% overlap (i.e., the width of the overlap region is ½ the slice width) between 17 and 18 is particularly advantageous for spiral scanning. By using overlapping axially slices in reconstructing MPR, 3D or CTA images the z-resolution of the resultant image is limited by the overlap increment and not the axial slice width. Therefore, for pitch=2 scanning the present invention can achieve z-spatial resolution up to ½ (slice width), while conventional scanners can only achieve z-spatial resolution of (slice width).

Figure 7A:
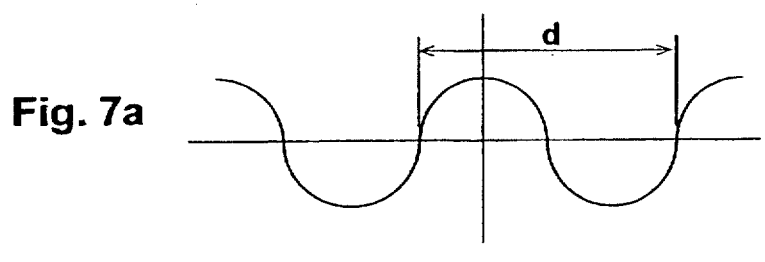
FIG. 7a is a diagram of the data acquisition for conventional spiral scanner.
Figure 7B:
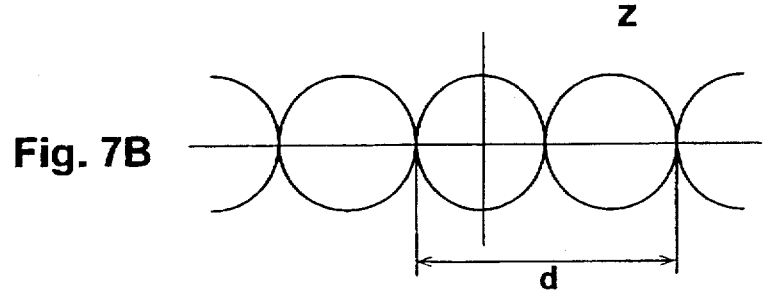
FIG. 7b is a diagram of the data acquisition for a spiral scanner of the present invention.

Referring now to FIG. 7a there is shown a data acquisition diagram for conventional spiral CT. Referring to FIG. 7b there is shown a data acquisition diagram for the present invention. In this case t has been selected such that the two sets of projection data are axially incremented by (d/2). For the case of pitch=1, d=½(slice width). Whereas for conventional spiral (with 360° LI) the data from a range of 2d is used, for the present invention (with 360° LI) the data from a range of d is used. The z-range of the projection data for present invention is one-half the z-range of projection data for conventional spiral scanners. The reduced range is a result of the double set of projection data that are measured from focal spot positions $z_1$ and $z_2$. The reduced z-range of projection data results is reduced broadening of the slice sensitivity profile.

Another advantage of the present invention relates to its application with 180° LI. For conventional scanners, with pitch=1, the 180° LI produces synthesized planar data from pairs of projection data that are acquired such that each the two projection measurements are acquired with the gantry 180° apart for each of the projection measurements. This synthesized data has inconsistencies due to the divergent beam effect of the x-ray beam resulting in partial volume artifacts. For the present invention, with pitch=1, all the interpolations are performed on projection data that are acquired from the same gantry rotation angle, thereby reducing data inconsistency from beam divergence.

It is obvious that the present invention may be used with dual slice spiral scanners, in addition to single slice scanners. The use of overlapping axial slices is now applied to pitch=4 with the same advantages as pitch=2 of single slice scanners. In addition, the reduction in the z-range of projection data required to synthesize planar projection data will result in reduced broadening of the slice sensitivity profile versus conventional dual slice scanners.

Whereas particular embodiments of the invention have been described above for the purposes of illustration it will be evident to those skilled in the art that numerous variations of details may be made without departing from the invention as defined in the appended claims.

Having thus described the preferred embodment, the invention is now claimed to be:

1. A CT scanner comprising:

a table for supporting and translating, along a z-axis through an examination region, an object that attenuates penetrating radiation;

an x-ray tube including a rotating anode having a surface impinged by an electron beam and generating X-rays at focal spots where so impinged by the electron beam;

said anode of the x-ray tube containing multiple radially-oriented sectors, wherein all sectors have indentical widths, adjacent sectors are of different thicknesses, and every other sector is of identical thickness such that a focal spot formed on the anode surface from the electron beam varies between two z-axis positions as the anode rotates;

beam collimation means producing a thin, fan beam shaped radiation beam for the two different z-axis positions of the beam;

radiation detection means for detecting the radiation that has traversed the object;

motor means for rotating the x-ray tube and radiation detector means through a multiplicity of angular positions around the object;

motor speed control means to rotate the anode at selected velocities;

speed designating means for designating angular velocities of the anode to the motor in accordance with the angular velocity of the x-ray tube and radiation detector;

means for acquiring projection measurements such that each projection measurement is with a known z-axis position of the focal spot and rotation angle of x-ray tube and radiation detector;

and reconstructing means for reconstructing image representations from the radiation detected by the detectors.

2. The CT scanner as set forth in claim 1 including projection data interpolation means such that the projection data for image reconstruction is interpolated from projection data obtained from two different z-positions of the x-ray beam.

3. The CT scanner as set forth in claim 1 including means for varying the rotation velocity of the anode in accordance with the angular position of the radiation beam such that radiation beams at two z-axis positions are generated at selected radiation beam rotation angles.

4. The CT scanner as set forth in claim 1 wherein said radiation detection means includes two abutting rows of radiation detectors.

5. The CT scanner as set forth in claim 1 wherein said reconstructing means reconstructs MPR, 3D and CTA images utilizing CT images reconstructed from projection data that are axially incremented by (½) the slice width to produce two sets of projection data simultaneously in an interlaced manner.

* * * * *